United States Patent [19]
Morelli et al.

[11] Patent Number: 6,140,492
[45] Date of Patent: Oct. 31, 2000

[54] ANTISENSE TRANSCRIPT EXPRESSED IN B LYMPHOCYTES AND SYNTHETIC OLIGONUCLEOTIDES USEFUL TO INHIBIT THE ACTIVITY THEREOF

[75] Inventors: Susanna Morelli; Angelo Nicolin, both of Milan; Alessandro Quattrone, Florence, all of Italy

[73] Assignee: Consiglio Nazionale Delle Richerche, Rome, Italy

[21] Appl. No.: 08/894,736

[22] PCT Filed: Mar. 1, 1996

[86] PCT No.: PCT/EP96/00853

§ 371 Date: Apr. 6, 1998

§ 102(e) Date: Apr. 6, 1998

[87] PCT Pub. No.: WO96/27664

PCT Pub. Date: Sep. 12, 1996

[30] Foreign Application Priority Data

Mar. 3, 1997 [IT] Italy .................................. MI95A1419

[51] Int. Cl.[7] ............................. C07H 21/04; C07H 21/02
[52] U.S. Cl. ...................... 536/24.5; 536/23.1; 536/24.1; 435/6; 435/455
[58] Field of Search ................................ 435/6, 440, 455; 514/44; 536/23.1, 24.1, 24.5

[56] References Cited

FOREIGN PATENT DOCUMENTS

WO 93/10138  5/1993  WIPO .
WO 93/24653  12/1993 WIPO .

OTHER PUBLICATIONS

M. Neurath et al., "The Murine Ig 3'αEnhancer is a Target Site with Repressor Function for the B Cell Lineage–Specific Transcription Factor BSAP (NF–HB, Sα–BP)", Journal of Immunology, 153 (2) :730–742 (1994).

T. Tanaka et al., "An Antisense Oligonucleotide Complementary to a Sequence in I 2bγIncreases γ2b Germline Transcripts, Stimulates B Cell DNA Synthesis and Inhibits Immunoglobulin Secretion", J. Exp. Med., 175 (2) :597–607 (1992).

Branch et al. "A Good Antisense Molecule is Hard to Find" TIBS vol. 23:45–50, Feb. 1998.

Agrawal S. "Antisense Oligonucleotides: Towards Clinical Trials" TIBTECH vol. 14:376–387, Oct. 1996.

*Primary Examiner*—Remy Yucel
*Assistant Examiner*—Sean McGarry
*Attorney, Agent, or Firm*—Oblon, Spivak, McClelland, Maier & Neustadt, P.C.

[57] ABSTRACT

An antisense transcript which complements the immature mRNA of the IgH gene, originates in the 3' region downstream the enhancer region (E) and terminates in the 5' region upstream the J region.

Oligodeoxynucleotides directed to any region of said antisense transcript and their use for diagnostic or pharmaceutical purposes.

29 Claims, 5 Drawing Sheets

SEQUENCE LISTING

```
<160> NUMBER OF SEQ ID NOS: 23

<210> SEQ ID NO 1
<211> LENGTH: 18
<212> TYPE: DNA
<213> ORGANISM: Homo sapiens

<400> SEQUENCE: 1
actactacgg tatggacg                                              18

<210> SEQ ID NO 2
<211> LENGTH: 18
<212> TYPE: DNA
<213> ORGANISM: Homo sapiens

<400> SEQUENCE: 2
tcctcaggta agaatggc                                              18

<210> SEQ ID NO 3
<211> LENGTH: 18
<212> TYPE: DNA
```

-continued

<213> ORGANISM: Homo sapiens

<400> SEQUENCE: 3
accatgttcc gagggac                                                18

<210> SEQ ID NO 4
<211> LENGTH: 18
<212> TYPE: DNA
<213> ORGANISM: Homo sapiens

<400> SEQUENCE: 4
gagccacatt tggacgag                                               18

<210> SEQ ID NO 5
<211> LENGTH: 18
<212> TYPE: DNA
<213> ORGANISM: Homo sapiens

<400> SEQUENCE: 5
agtgatggct gaggaatg                                               18

<210> SEQ ID NO 6
<211> LENGTH: 18
<212> TYPE: DNA
<213> ORGANISM: Homo sapiens

<400> SEQUENCE: 6
ctgtccaagt atttgaaa                                               18

<210> SEQ ID NO 7
<211> LENGTH: 18
<212> TYPE: DNA
<213> ORGANISM: Homo sapiens

<400> SEQUENCE: 7
ggctggaaag agaactgt                                               18

<210> SEQ ID NO 8
<211> LENGTH: 18
<212> TYPE: DNA
<213> ORGANISM: Homo sapiens

<400> SEQUENCE: 8
tctgaaagtg atctactg                                               18

<210> SEQ ID NO 9
<211> LENGTH: 18
<212> TYPE: DNA
<213> ORGANISM: Homo sapiens

<400> SEQUENCE: 9
ttgcgtttct aaaataag                                               18

<210> SEQ ID NO 10
<211> LENGTH: 18
<212> TYPE: DNA
<213> ORGANISM: Homo sapiens

<400> SEQUENCE: 10
gatgcgtggc ttctgctg                                               18

<210> SEQ ID NO 11
<211> LENGTH: 21

```
<212> TYPE: DNA
<213> ORGANISM: Homo sapiens

<400> SEQUENCE: 11
ctagggcctt tgttttctgc t                                              21

<210> SEQ ID NO 12
<211> LENGTH: 21
<212> TYPE: DNA
<213> ORGANISM: Homo sapiens

<400> SEQUENCE: 12
gcgatcttgc agtcctacag a                                              21

<210> SEQ ID NO 13
<211> LENGTH: 18
<212> TYPE: DNA
<213> ORGANISM: Homo sapiens

<400> SEQUENCE: 13
cgtccatacc gtagtagt                                                  18

<210> SEQ ID NO 14
<211> LENGTH: 18
<212> TYPE: DNA
<213> ORGANISM: Homo sapiens

<400> SEQUENCE: 14
gccattctta cctgagga                                                  18

<210> SEQ ID NO 15
<211> LENGTH: 18
<212> TYPE: DNA
<213> ORGANISM: Homo sapiens

<400> SEQUENCE: 15
cgaaccggga tggacttc                                                  18

<210> SEQ ID NO 16
<211> LENGTH: 18
<212> TYPE: DNA
<213> ORGANISM: Homo sapiens

<400> SEQUENCE: 16
ctcgtccaaa tgtggctc                                                  18

<210> SEQ ID NO 17
<211> LENGTH: 18
<212> TYPE: DNA
<213> ORGANISM: Homo sapiens

<400> SEQUENCE: 17
acagttctct ttccagcc                                                  18

<210> SEQ ID NO 18
<211> LENGTH: 18
<212> TYPE: DNA
<213> ORGANISM: Homo sapiens

<400> SEQUENCE: 18
gagcaggttt acaccgag                                                  18

<210> SEQ ID NO 19
```

-continued

```
<211> LENGTH: 18
<212> TYPE: DNA
<213> ORGANISM: Homo sapiens

<400> SEQUENCE: 19
gtcccctcgg aacatggt                                                 18

<210> SEQ ID NO 20
<211> LENGTH: 18
<212> TYPE: DNA
<213> ORGANISM: Homo sapiens

<400> SEQUENCE: 20
cagtagagca ctttcaga                                                 18

<210> SEQ ID NO 21
<211> LENGTH: 18
<212> TYPE: DNA
<213> ORGANISM: Homo sapiens

<400> SEQUENCE: 21
cagcagaagc cacgcatc                                                 18

<210> SEQ ID NO 22
<211> LENGTH: 20
<212> TYPE: DNA
<213> ORGANISM: Homo sapiens

<400> SEQUENCE: 22
aaccccactg aaaaagatga                                               20

<210> SEQ ID NO 23
<211> LENGTH: 20
<212> TYPE: DNA
<213> ORGANISM: Homo sapiens

<400> SEQUENCE: 23
atcttcaaac ctccatgatg                                               20
```

ANTISENSE TRANSCRIPT EXPRESSED IN B LYMPHOCYTES AND SYNTHETIC OLIGONUCLEOTIDES USEFUL TO INHIBIT THE ACTIVITY THEREOF

This invention relates to an antisense transcript expressed in normal and leukemic B lymphocytes and to synthetic oligodeoxynucleotides (ODN) useful to inhibit the activity of said antisense transcript, thus causing the increased synthesis of immunoglobulins and the death of tumoral cells.

More particularly, this invention relates to an endogenous antisense transcript that complements the pre-mRNA (immature RNA) of the gene coding for the heavy chain of immunoglobulins (IgH), thus exerting a negative control action on the immunoglobulins production.

It is well known that the synthetic oligodeoxynucleotides are short single strand DNA chains. The nucleotide sequence is ordered in a specular fashion to complement the correspondent nucleotide sequence within the mRNA to be inhibited. By that modality they are capable of regulating gene expression in a specific way.

It is important that the oligodeoxynucleotides have a length suitable to optimally hybridize the target mRNA. In general, the minimum length is of 10 and the maximum length is of 100 bases. Preferably, 15–30 bases is the most used length; most preferably the length is of 18 bases since statistical analysis teaches that each sequence of such a length is unique in the human genome.

The oligodeoxynucleotides can act at different steps of the mRNA metabolic pathway, either at nuclear or at cytoplasmic level. It is moreover likely that oligodeoxynucleotides might act at the ribosome level, or straight at the DNA level both in the nucleus and in the mitochondria. The nucleotide length of oligodeoxynucleotides may be selected also in view of the basic knowledge of the person skilled in the art concerning the efficiency in crossing the cellular membranes (Locke S. L. et al.: Mechanism of oligonucleotide uptake by cells: involvement of specific receptors? *Proc. Natl. Acad. Sci. USA* 86:3474, 1989. Yakubov L. A. et al.: Characterization of oligonucleotide transport into living cells. *Proc. Natl. Acad. Sci. USA* 86:6454, 1989).

It is also known that discrete regions within specific genes may be transcribed in both directions. More commonly, a single strand (positive) from the double strand is transcribed into mRNA and afterwards translated into protein. In some circumstances, however, the negative strand may also be transcribed (endogenous antisense RNA), playing a regulatory role in the functions of the regular transcript. The antisense transcripts may regulate the synthesis, maturation, stability and translation of the messenger RNA (Green P. J. et al.: The role of antisense RNA in gene regulation. *Ann. Rev. Biochem.* 55:569, 1990; Krystal G. W. et al.: N-myc mRNA forms RNA-RNA duplex with endogenous antisense transcripts. *Mol. Cell Biol.* 10:4180, 1990; Taylor E. R. et al.: identification of antisense transcripts of the chicken insulin-like growth factor-II gene. *J. Mol. Endocrinol.* 7:145, 1991).

Finally, it is known that the locus coding for the heavy chain of the immunoglobulins (IgH) is composed of sub-loci which undergo an ordered rearrangement during the lymphocyte maturation originating the mature IgH gene. It includes the V region (variable), the D region (diversity), the J region (joining). The above gene segments code for the variable region of the heavy chain of the immunoglobulins and, in the course of the rearrangement, they may loose nucleotides at the extremities of the junction and/or addition of random nucleotides that originate new nucleotide sequences, called N regions, that contribute for the hypervariation regions of the antibodies.

Upstream to each V segment is located a promoter that is activated upon the segment is rearranged. The promoter is under the influence of the Enhancer sequence (E) located between the J segment and the constant (C) region (FIG. 1).

The sequence of the IgH gene has been already reported in the literature and it is known that the breaking points of the IgH locus are mainly located within the J region (Ravetch J. V. et al.: Structure of the human immunoglobulin locus: characterization of embryonic and rearranged J and D genes. *Cell* 27:583, 1981).

Moreover, the enhancer nucleotide sequence is stored in the European Molecular Biology Laboratory (EMBL) Data bank, Accession number x54712 as published by Sun Z. et al. ("Sequencing of selected regions of the human immunoglobulin heavy-chain gene locus that completes the sequence from Jh through the delta constant region. DNA sequence J DNA sequencing and mapping 1:347, 1991).

Figure 1:
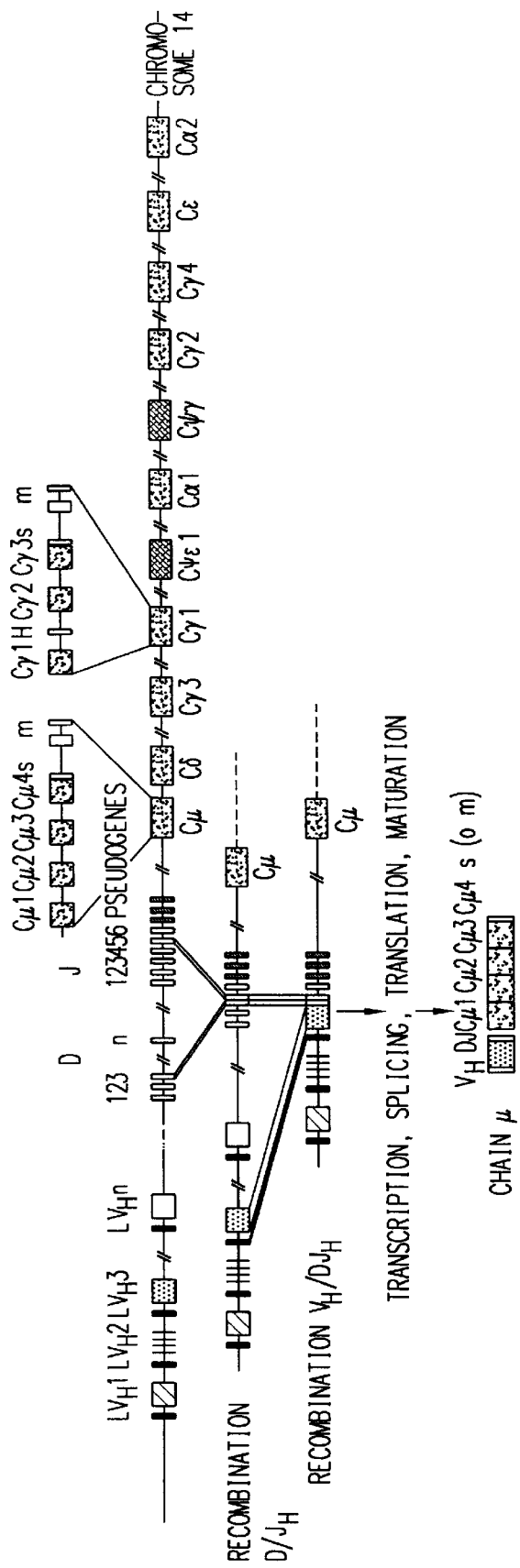
FIG. 1 depicts the rearrangements events in the IgH locus.
Figure 2:
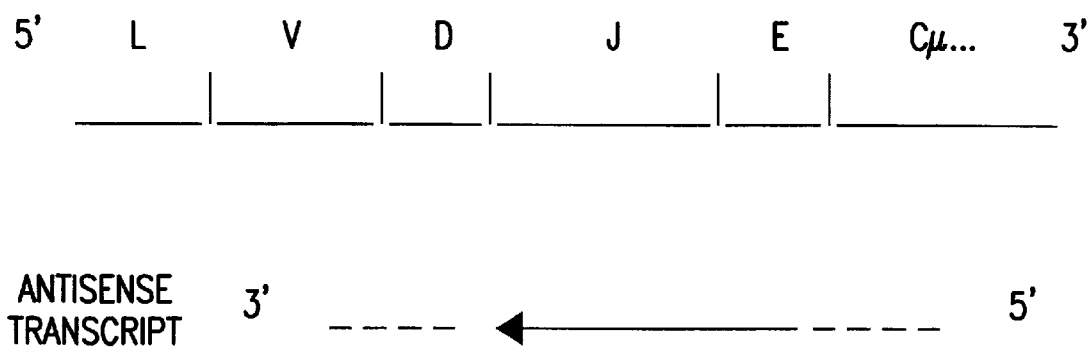
FIG. 2 depicts the immature immunoglobulin mRNA and the antisense transcript.

Now, we have found that in B lymphocytes it is expressed an antisense transcript that originates in the proximity of the enhancer region and terminates upstream the J region (FIG. 2) and that said antisense transcript play a regulatory role in the antibody synthesis by inhibiting the pre-mRNA maturation of the regular transcript, thus causing a reduction in the antibodies synthesis.

The finding, by the inventors, of the above mentioned endogenous antisense transcript is very relevant also because its nucleotide sequence is easily deducible from the complementary Immature mRNA.

In turn, the knowledge of the nucleotide sequence of the antisense transcript allows to design and prepare, by easy technologies well known to the persons skilled in the art, sense-oriented oligodeoxynucleotides capable of hybridizing the above mentioned antisense transcript, thus causing the destabilization of the antisense transcript and increasing the production of immunoglobulins from B lymphocytes.

It is therefore a first object of the present invention to provide an antisense transcript complementing the immature regular mRNA within the IgH mRNA characterized in that it a) originates 3' downstream the enhancer region and terminates 5' upstream the J region, and b) hybridizes with an oligodeoxynucleotide selected form the group comprising ACT ACT ACG GTA TGG ACG (SEQ ID NO: 1),
TCC TCA GGT AAG AAT GGC (SEQ ID NO: 2),
ACC ATG TTC CGA GGG GAC (SEQ ID NO: 3),
GAG CCA CAT TTG GAC GAG (SEQ ID NO: 4),
AGT GAT GGC TGA GGA ATG (SEQ ID NO: 5),
CTG TCC AAG TAT TTG AAA (SEQ ID NO: 6), GGC TGG AAA GAG AAC TGT (SEQ ID NO: 7),
TCT GAA AGT GAT CTA CTG (SEQ ID NO: 8),
TTG CGT TTC TAA AAT AAG (SEQ ID NO: 9) or
GAT GCG TGG CTT CTG CTG (SEQ ID NO: 10).

A second object of the present invention is to provide a sense-oriented oligodeoxynucleotide, optionally chemically modified in order to increase their activity in vivo, which inhibits the action of the above mentioned endogenous antisense transcript.

The above mentioned sense-oriented oligodeoxynucleotide may be designed to complement the E region or the J region as well.

Typical examples of oligodeoxynucleotides complementary to the J6 region of the IgH mRNA comprise the following sequences:

ACT ACT ACG GTA TGG ACG (SEQ ID NO: 1)
(from nucleotite 2956 to nucleotide 2973)
TCC TCA GGT AAG AAT GGC (SEQ ID NO: 2)
(from nucleotide 3003 to nucleotide 3020)
ACC ATG TTC CGA GGG GAC (SEQ ID NO: 3)
(from nucleotide 3119 to nucleotide 3136)

Typical examples of ODN that hybridize with the J6/E region (between the J6 segment and the enhancer) comprise the following sequences:

GAG CCA CAT TTG GAC GAG (SEQ ID NO: 4)
(from nucleotide 3272 to nucleotide 3289)
AGT GAT GGC TGA GGA ATG (SEQ ID NO: 5)
(from nucleotide 3314 to nucleotide 3331)
CTG TCC AAG TAT TTG AAA (SEQ ID NO: 6)
(from nucleotide 3776 to nucleotide 3783)
GGC TGG AAA GAG AAC TGT (SEQ ID NO: 7) (from nucleotide 3459 to nucleotide 3476)

Typical examples of ODN that hybridize with the E region are:

TCT GAA AGT GAT CTA CTG (SEQ ID NO: 8)
(from nucleotide 3524 to nucleotide 3541)
TTG CGT TTC TAA AAT AAG (SEQ ID NO: 9) (from nucleotide 3564 to nucleotide 3581)
GAT GCG TGG CTT CTG CTG (SEQ ID NO: 10)
(from nucleotide 4218 to nucleotide 4235)

In the present description and in the claims attached hereto, the expression "modified in order to improve the in vivo activity" means those chemical modifications which are known to the person skilled in the art to increase the crossing of the cellular membranes and/or improve the stability of the oligodeoxynucleotides to the attacks of the exo and endo-nucleases without altering the capability of hybridizing the target mRNA (Uhlmann E. et al.: Antisense oligonucleotides: a new therapeutic principle. *Chemical Rev* 90:544, 1990).

Typical examples of structural modifications capable of increasing the stability to nucleases are those involving the phosphorous group. For instance, methylphosphonates, phosphoroamidates, phosphorotriesters, phosphorothioates and the phosphorodithioates.

Typical examples of chemical modifications that increase the membrane crossing involves utilizing lipophilic compounds, preferably cholesterol, that usually are covalently bound by a methylene bridge (at the 5' or at the 3' termination or both).

The oligodeoxynucleotides of the present invention can be easily prepared in solid phase by means of techniques well known to the person skilled in the art, such as those reported by Narang A. (*Tetrahedron* 39:3, 1983), by Itakura K. (Synthesis and use of synthetic oligonucleotides. *Ann Rev Biochem* 53:323 1984), or in "Oligonucleotides Synthesis; A Practical Approach", Gait M. J. Ed. IRL Press, Oxford, UK, 1984).

If desired, the thus prepared oligodeoxynicleotides may be purified by conventional techniques such as, for instance, Polyacrilamide Gel Electrophoresis (PAGE) under denaturing conditions, High Performance Liquid Chromatography (HPLC) either in inverse phase or in ion-exchange column, and capillary chromatography.

The oligodeoxynucleotides of the present invention will be dispensed to human beings by administration routes and dosages which are selected according parameters well known to the person skilled in the art depending on the disease severity, the body weight, the specific oligodeoxynucleotide which is used, and the like.

In particular, they will cause a potentiation of the antibody response when so required such as, for instance, in case of vaccinations, in particular in immunodepressed and aged patients, or in any case of reduced antibody production even in case of no overt disease. They may be used even for preventive purposes, in particular in case of epidemics or during infections by pathogenic agents, including the viruses and the retro-viruses such as HIV virus. Moreover, they may be used as anti-leukemic compounds in case of cell leukemia or cell lymphoma of B lymphocytes origin.

They can be used also for diagnostic purposes to monitor the function of the antibody reaction and in case of B cell leukemia and lymphoma.

The following examples are given to better illustrate the present invention without, however, limiting it in any way.

EXAMPLE 1

Antisense Transcript in B Lymphocytes

Total mRNA extracted from B lymphocytes was separated in two plastic tubes and reverse-transcribed by using in the first tube the primer in sense orientation (primer A (SEQ ID NO: 11), 5'-CTA GGG CCT TTG TTT TCT GCT-3', from nucleotide 3025 to nucleotide 3045 within the J6 region) and, in a second tube, a primer in antisense orientation (primer B (SEQ ID NO: 12), 5'-GCG ATC TTG CAG TCC TAC AGA-3' from nucleotide 3348 to nucleotide 3369 within the region between the J6 and the enhancer).

The same procedure was followed by using the Jurkat cells (T cell lymphoma) and the Raji cells (B cell lymphoma).

The cDNA preparations were amplified via polymerase chain reaction (PCR) by adding the second primer to the first tube and the first primer to the second tube.

The amplification products were analyzed by agarose gel electrophoresis.

Figure 3:
FIG. 3 depicts amplification products of sense and antisense cDNAs in an agarose gel where it can be seen that both sense and antisense transcripts are found in both normal B lymphocytes and tumor B cell lines.
Figure 4A:
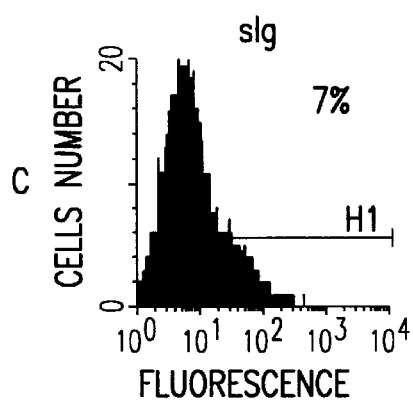
FIG. 4 depicts increase in the production of immunoglobulins with ODN 98.
Figure 4D:
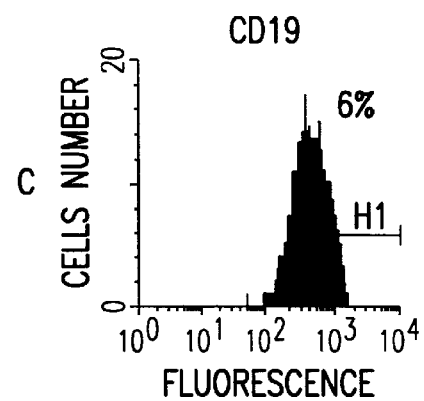
Figure 4B:
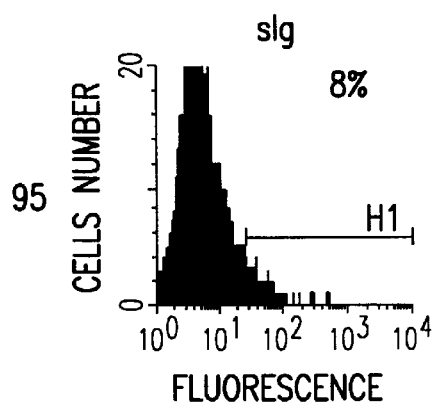
Figure 4E:
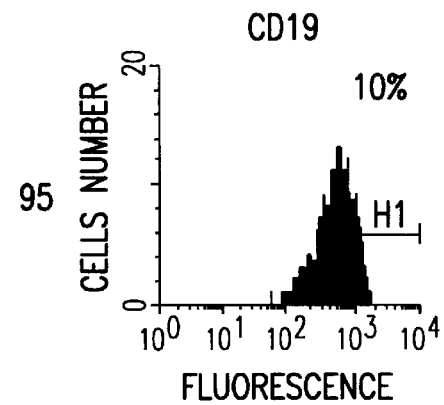
Figure 4C:
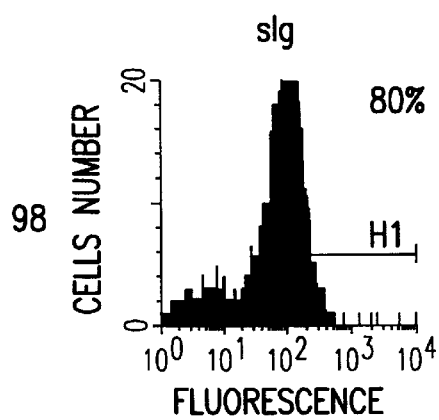
Figure 4F:
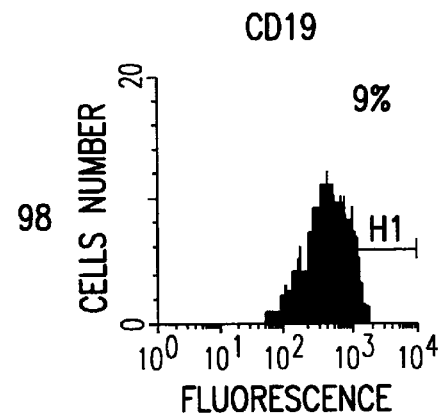

As shown in FIG. 3, two bands of the expected molecular weight, were easily detectable in the lanes related to the B lymphocytes and the Raji cells, one band corresponding to the sense transcript and the other to the antisense transcript (lane 4 Raji-sense cDNA, lane 5 Raji-antisense cDNA, lanes 6 and 7 are related to the sense and antisense cDNA from B lymphocytes). No band in the gel was found in the reverse transcribed mRNA extracted from the Jurkat cells, a T cell tumor line (lanes 8 and 9, sense and antisense cDNA from Jurkat cells). It is note-worthy that the antisense transcript was found in both normal B lymphocytes and tumor B cell lines. In particular, in these tumor lines, oligodeoxynucleotides complementary to whatever region of the antisense transcript may be considered to possess antitumor activity since the over-stimulation (increased synthesis of immunoglobulins) induces the cell death by activating the programmed cell death (this occurs after about 5 days of treatment).

Further controls were carried out in order to exclude contaminations from genomic DNA, by digesting the mRNA of the cell lines under investigation with the enzyme RNaseA (in the Figure, lanes 1-2-3) before the reverse-transcription.

EXAMPLE 2

Oligodeoxynucleotide Preparation

The synthesis was performed according to the chemistry of the beta-cyanoethyl-phosphoroamidates in solid phase with a Perkin-Elmer ABI 392 equipment.

Upon removal from the resin, the oligodeoxynucleotide was deprotected with 30% ammonia in 12 hours at 55° C.

Purification was carried out on a chromatography column NAP 25 (Sephadex G25) from Pharmacia Biotech.

The column NAP 25 had been balanced with 4×5 ml of 20% ethanol buffer and crude oligodeoxynucleotide was eluted with the 20% ethanol buffer.

The eluted fraction was collected and dried after spectrofluorimetric determination (260 and 280 nm) of the concentration.

With this procedure were prepared the following oligodeoxynucleotides:

ACT ACT ACG GTA TGG ACG (SEQ ID NO: 1)
TCC TCA GGT AAG AAT GGC (SEQ ID NO: 2)
ACC ATG TTC CGA GGG GAC (SEQ ID NO: 3)
GAG CCA CAT TTG GAC GAG (SEQ ID NO: 4)
AGT GAT GGC TGA GGA ATG (SEQ ID NO: 5)
CTG TCC AAG TAT TTG AAA (SEQ ID NO: 6)
GGC TGG AAA GAG AAC TGT (SEQ ID NO: 7)
TCT GAA AGT GAT CTA CTG (SEQ ID NO: 8)
TTG CGT TTC TAA AAT AAG (SEQ ID NO: 9)
GAT GCG TGG CTT CTG CTG (SEQ ID NO: 10) as well as the following primers:
5' CTA GGG CCT TTG TTT TCT GCT 3' (SEQ ID NO: 11)
5' GCG ATC TTG CAG TCC TAC AGA 3' (SEQ ID NO: 12) and the following control oligodeoxynucleotides:
CGT CCA TAC CGT AGT AGT (SEQ ID NO: 13)
GCC ATT CTT ACC TGA GGA (SEQ ID NO. 14)
CGA ACC GGG ATG GAC TTC (SEQ ID NO: 15)
CTC GTC CAA ATG TGG CTC (SEQ ID NO: 16)
ACA GTT CTC TTT CCA GCC (SEQ ID NO: 17)
GAG CAG GTT TAC ACC GAG (SEQ ID NO: 18)
GTC CCC TCG GAA CAT GGT (SEQ ID NO: 19)
CAG TAG AGC ACT TTC AGA (SEQ ID NO: 20)
CAG CAG AAG CCA CGC ATC (SEQ ID NO: 21)

EXAMPLE 3

In Vitro Activity of Oligodeoxynucleotides Against the Antisense Transcript in the B Lymphocytes In this assay the following oligodeoxynucleotides of the invention directed against the J6, J6/E and E of the antisense transcript, were used.

ODN 96 ACT ACT ACG GTA TGG ACG (SEQ ID NO: 1)
(from nucleotide 2956 to nucleotide 2973)
ODN 97 TCC TCA GGT AAG AAT GGC (SEQ ID NO: 2)
(from nucleotide 3003 to nucleotide 3020)
ODN 98 ACC ATG TTC CGA GGG GAC (SEQ ID NO: 3)
(from nucleotide 3119 to nucleotide 3136)
ODN 104 GAG CCA CAT TTG GAC GAG (SEQ ID NO: 4)
(from nucleotide 3272 to nucleotide 3289)
ODN 105 AGT GAT GGC TGA GGA ATG (SEQ ID NO: 5)
(from nucleotide 3314 to nucleotide 3331)
ODN 106 CTG TCC AAG TAT TTG AAA (SEQ ID NO: 6)
(from nucleotide 3776 to nucleotide 3783)
ODN 107 GGC TGG AAA GAG AAC TGT (SEQ ID NO: 7)
(from nucleotide 3459 to nucleotide 3476)
ODN 115 TCT GAA AGT GAT CTA CTG (SEQ ID NO: 8)
(from nucleotide 3524 to nucleotide 3541)
ODN 116 TTG CGT TTC TAA AAT AAG (SEQ ID NO: 9)
(from nucleotide 3564 to nucleotide 3581)
ODN 118 GAT GCG TGG CTT CTG CTG (SEQ ID NO. 10)
(from nucleotide 4218 toal nucleotide 4235)
as well as the following control oligodeoxynucleotides:
CGT CCA TAC CGT AGT AGT (SEQ ID NO: 13)
(ODN 102=antisense of the ODN 96)
GCC ATT CTT ACC TGA GGA (SEQ ID NO: 14)
(ODN 103=antisense of the ODN 97)
CGA ACC GGG ATG GAC TTC (SEQ ID NO: 15)
(ODN 100=ODN 98 scramble)
CTC GTC CAA ATG TGG CTC (SEQ ID NO: 16)
(ODN 120=antisense of the ODN 104)
ACA GTT CTC TTT CCA GCC (SEQ ID NO: 17)
(ODN 108=antisense of the ODN 107)
GAG CAG GTT TAC ACC GAG (SEQ ID NO: 18)
(ODN 121=ODN 104 inverted)
GTC CCC TCG GM CAT GGT (SEQ ID NO: 19)
(ODN 99=antisense OF THE ODN 98)
CAG TAG AGC ACT TTC AGA (SEQ ID NO: 20)
(ODN 130=antisense of the ODN 115)
CAG CAG AAG CCA CGC ATC (SEQ ID NO: 21)
(ODN 119=antisense of the ODN 118)

a) Normal B lymphocytes

To assay the activity, normal human B lymphocytes obtained from children tonsils were used.

After disgregation of the tonsils in a Petri dish (under sterile conditions), the supernatant was collected and centrifuged 10 min. at 1,500 rpm.

The pellet was resuspended in complete RPMI 1640 and centrifuged in Ficoll. The cells, resuspended in complete culture medium, were treated with antibodies to the T lymphocyte membranes (CD3, CD2, and CD14 for the human macrophages) and left 30 min. at 4° C. The cells were washed twice in complete RPMI and resuspended at the desired concentration.

The separation of T cells from B cells was performed by Dynabeads conjugated with goat-anti mouse IgG. (Dynabeads M-450 Goat-Anti-Mouse Unipath). After washing with RPMI in order to remove sodium azide, the microspheres were added to the cell suspension following a defined ratio cells/microbeads as indicated by the kit. Then the cells were left in an ice bath for 30 min. under gentle stirring, from time to time, to allow a constant contact of the cells with the microbeads.

The microbeads associated with the B lymphocytes were removed by the use of a magnet and a cottoned pasteur pipette. This operation was repeated twice in order to remove any remaining microsphere.

After a short washing, the cells were resuspended with RPMI added with 10% FCS (complemented at 65° C.) plus antibiotics and glutamine.

The thus obtained B lymphocytes were seeded (700,000 per well) in Costar plates, 24 wells, and exposed three days to the above mentioned oligodeoxynucleotides: at day zero the oligodeoxynucleotides of the present invention were added both at 10 $\mu$M and 1 $\mu$M. In the following days the cell cultures were added with half the dose of oligodeoxynucleotides. Moreover, there were used the control oligodeoxynucleotides to check the specificity of the oligodeoxynucleotides of this invention.

The activity was tested by staining the fluorescent antibodies anti IgG, anti IgM, anti IgA and anti IgD (Mouse anti-human).

The fluorescence intensity was measured by an automatic cytofluorimeter.

The oligodeoxynucleotides of this invention showed a clear capability of increasing the membrane fluorescence, that indicates an increase in the production of immunoglobulins. No increased fluorescence was seen in the cell samples treated with control oligodeoxynucleotides (FIG. 4). As a positive control it was used the fluorescinated antibody anti-CD19 that recognizes a membrane receptor of B lymphocytes.

Moreover, it was evaluated (Elisa test) the amount of IgM and IgG released in the medium culture.

The well coating was performed with 100 $\mu$l/well in flat-bottom plates (Covalink-Nunc) of anti IgM or anti IgG of mouse anti-human antibodies at the concentration of 10 $\mu$g/ml diluted in PBS at pH 7.4. PBS had been prepared by dissolving 8 g of NaCl, 0.2 g of $KH_2PO_4 \times 12 \ H_2O$ and 0.2 g of KCl in 1 liter of deionized water by adjusting pH at 7.4 and keeping the temperature at 4° C. (the reagents used in this preparation had been supplied by MERK).

The plate was incubated one night at 4° C. Afterwards, the plate was washed 4 times with 200 $\mu$l of washing solution (PBS+0.2% Tween 20) (MERK) and dried.

In each well, there were added 200 $\mu$l of 1% bovine albumin (BSA) in PBS (SIGMA). After 60 min. incubation at 37° C., the wells were washed 4 times with the above mentioned washing solution.

At this point, 50 $\mu$l per well of the supernatant were tested as to the content of IgM and IgG. In all the wells, 100 $\mu$l of mouse anti-human conjugated with alkaline phosphatase (ZYMED) diluted 1:2,000 in PBS+0.1% BSA were added. After 60 min. incubation at 37° C. and 4 times washings as described above, in the wells there were added 100 $\mu$l of a substrate consisting of paranitrophenylphosphate (PNPP) (1 mg/ml, SIGMA) dissolved in a diethanolammine buffer, at pH 9.8, prepared from a solution of 97 ml of diethanolammine (SIGMA), 800 ml of distilled water, 0.1 g of $MgCl_2 6H_2O$ (SIGMA), and adjusted at pH 9.8 with concentrated hydrochloric acid (SIGMA) added with 0.02% of sodium azide (MERCK) and distilled water up to 1 liter.

The substrate was incubated 60 min. at 37° C. Then the reaction was stopped by adding 50 $\mu$l per well of sodium hydroxyde 3 M and the optical density of the supernatants from the treated cells was measured at 405 nm by a TITERTEK reader from Flow Lab. The results were comparable to those obtained by the cytofluorimetric assays. Therefore, the oligodeoxynucleotides of the present invention may be used in the production of antisera.

When designed to complement the variable regions of the immunoglobulins, oligodeoxynucleotides can work in a selective way via stimulation of specific cell clones.

b) Tumor B cells

It was proved that the antisense transcript negatively regulates the antibody production and that it is present in tumor B cells. Therefore, by treating these cells with suitable doses of the oligodeoxynucleotides of this invention directed to any region of the antisense transcript, the antibody production is stimulated. However, at a higher stimulation level (i.e. at a higher concentration), the cells activate their own programmed death.

This was observed by treating for 5 days both normal and tumor B cells with the oligodeoxynucleotides of this invention directed to any various region of the antisense transcript.

Tumor B cells (Raji and Daudi) and non B cells (Jurkat, K562 and HL60) were maintained in culture with RPMI added with 10% FCS (scomplemented at 56° C.), antibiotic and glutamine, and incubated at 37° C. in a moist atmosphere of $CO_2$ and 95% humidity. Before any treatment with oligodeoxynucleotides, the cells were washed twice with HBSS to remove any trace of FCS. Then the cells were resuspended in RPMI with FCS scomplemented at 65° C. to remove the nucleases capable to degrade the oligodeoxynucleotide.

10,000 cells were seeded in each well of flat-bottom plates having 96 wells and treated with the oligodeoxynucleotides of this invention both at a concentration of 10 $\mu$l and 1 $\mu$l for 5 days: at the day 0 it was administered the entire dose, followed by half dose in the following days.

Controls were performed by treating the cells with non-related or random oligodeoxynucleotides.

The oligodeoxynucleotides activity was detected by both observation under an inverted microscope of the morphological appearance of the cells treated with the oligodeoxynucleotides (the cells which have activated their own programmed death have a reduced volume and show a peculiar bebbling of the cytoplasmic membrane) and cells count under an optical microscope followed by counting of the radioactivity incorporated into the nuclei by adding tritiated Thymidine, 1 mC/ml.

At a concentration of 10 $\mu$l, the sense oriented oligodeoxynucleotides proved to decrease both the cells number and the radioactivity incorporated into the cell nuclei.

Figure 5:
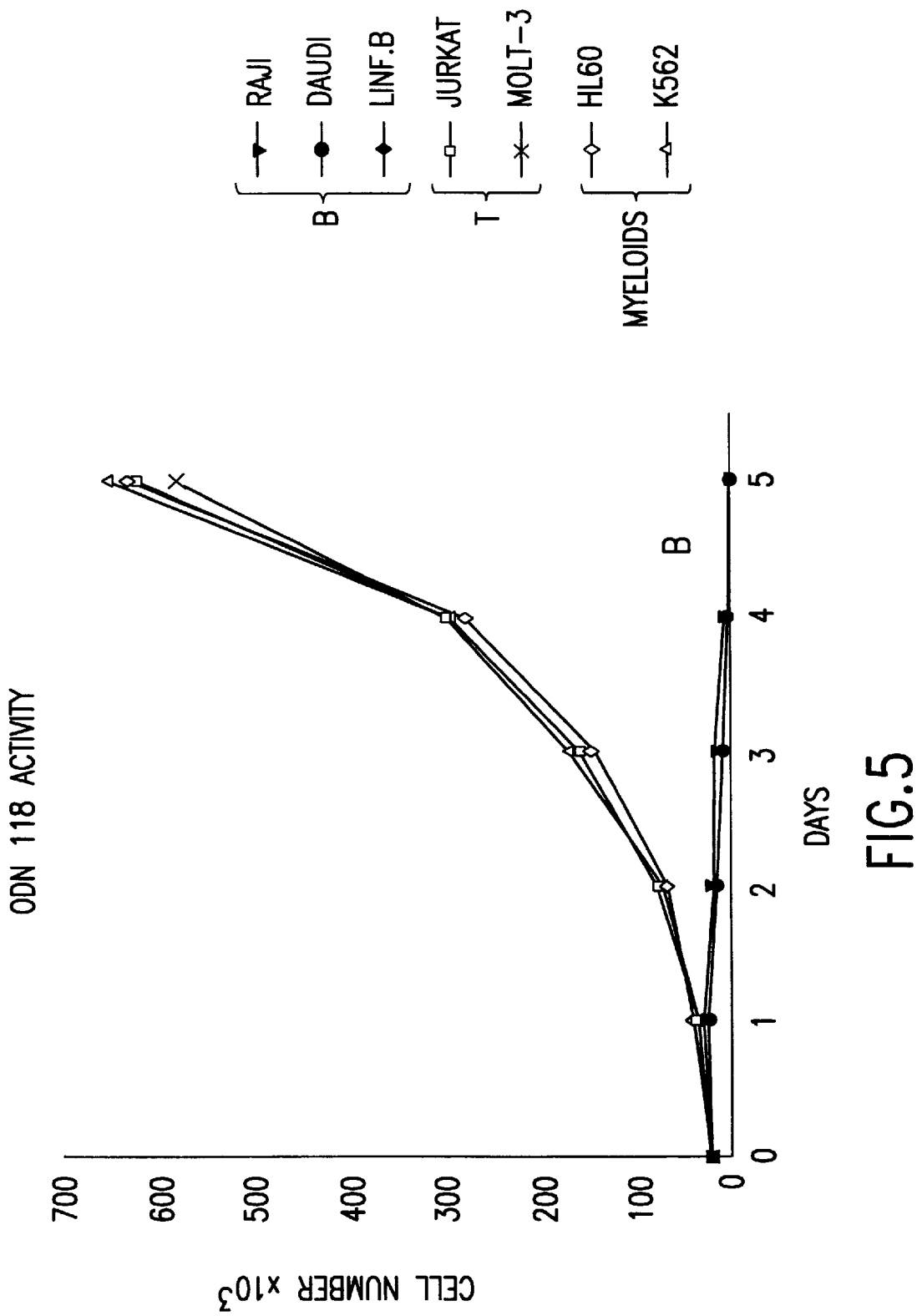
FIG. 5 depicts the activity of ODN 118.

As shown in FIG. 5 due to the treatment with the sense oligodeoxynucleotides, B cell lines are induced to die while the non B cells can grow exponentially and show no difference compared to the cells which have not been treated with oligodeoxynucleotides.

EXAMPLE 4 mRNA Determination

The increased production of immunoglobulins due to the treatment with the sense oriented oligodeoxynucleotides directed to any region of the antisense transcript were evaluated by quantitating the mRNA coding for the IgM of the B lymphocytes exposed to the oligodeoxynucleotides of the present invention.

The quantitation was performed by the RT-PCR assay (Reverse Transcriptase-Polymerase Chain Reaction) as described by Horikoshi T. et al. ("Quantitation of Thymidilate Synthase, Dihydrofolate reductase and DT-diaphorAse gene expression in human tumors using polymerase chain reaction. *Cancer Res.* 52:108, 1992).

The total RNA extracted from the cells by the RNAzol B method (CINNA BIOTECX, Houston, Tex., USA), treated with DNase and proteinase K, was reverse transcribed into cDNA by the Mo-MLV reverse transcriptase (PROMEGA, Madison, Wis.) and random examiners (RX). With proper primers IgM, beta actin, microglobulin 2, as internal standards, were amplified from the same cDNA by PCR in the presence of radioactive ATP. PCR was performed in the presence of AmpliTaq (PERKIN-ELMER, Norwalk, Conn.) by using increasing amount of cDNA and the following primers (GENOSIS, Cambridge, England):

$_2$mA, 5' AAC CCC ACT GAA GAT GA 3' (SEQ ID NO: 22)

from nucleotide 1544 to 1563 of the $\beta_2$m gene, $_2$mB, 5' ATC TTC AAA CCT CCA TGA TG 3' (SEQ ID NO: 23)

from nucleotide 2253 to 2262 of the β2m gene (Noonan K E, "Quantitative analysis of MDR1 (multidrug resistance) gene expression in human tumors by polymerase chain reaction" *Proc Natl Acad Sci USA*, 87:7160, 1990)

J6 5' CTA GGG CCT TTG TTT TCT GCT 3' (SEQ ID NO: 11)

from nucleotide 3025 to nucleotide 3045,

J6/E 5' GCG ATC TTG CAG TCC TAC AGA 3' (SEQ ID NO: 12)

from nucleotide 3348 to 3369.

After 30 cycles of PCR the amplification products were quantitated by counting the radioactivity in the scintillation liquid of the bands obtained from a 6% PAGE under non-denaturing conditions. The samples were analyzed by 1.5% agarose gel electrophoresis and quantitated by densitometry.

The amount of IgM mRNA was calculated as compared with β-actin and β$_2$microglobulin used as internal standard.

The thus obtained data, calculated as percent value of the untreated controls, show that sense oriented oligodeoxynucleotides decreased Immunoglobulin mRNA in a dose dependent fashion. Cells treated with control oligodeoxynucleotides did not show any content alteration in the immunoglobulin mRNA.

EXAMPLE 5

In vivo Activity of Oligodeoxynucleotides Against the Antisense Transcript in B Lymphocytes It was preliminary studied the growth of Raji lymphoma in immunodeficient mice (SCID). It is an autosomic spontaneous recessive mutation on chromosome 16 responsible for an alteration in the recombinant system which controls the correct rearrangement of the VDJ loci both in T and in B lymphocytes.

SCID mice lost the B and T functions while the Natural Killer activity is inactivated by antibodies to the asyalglicoprotein: therefore, in these mouse strains the transplantation of human tumors is successful. After checking the take of the Raji lymphoma injected iv in these mice, studies have been initiated to evaluate the therapeutic activity of a sense oriented oligodeoxynucleotide directed to the enhancer region of the immunoglobulin. Four mice carrying the Raji lymphoma were treated from day 1 to day 15 with 1 mg/day of the above mentioned oligodeoxynucleotide. A control 4 animal group carrying the same lymphoma were treated by the same modalities with the corresponding antisense oriented oligodeoxynucleotide. Four other animals, untreated controls, were treated with physiological solution.

The oligodeoxynucleotide and the physiological solution treatments were performed by an osmotic micropump (ALZET, Charles River), inserted subcutaneously to each mouse and containing the compound under evaluation. The pump released 1 mg/day for a total or 15 mg/mouse. In the group of animals treated with the sense oriented oligodeoxynucleotide it was obtained an increase in the medium survival time as compared with the survival of the animals treated with the antisense oriented oligodeoxynucleotide or the physiological solution.

What is claimed is:

1. An oligodeoxynucleotide which is complementary to an antisense transcript of an immature mRNA of the IgH gene, inhibits the activity of said antisense transcripts and has a base sequence consisting of a member selected from the group consisting of ACT ACT ACG GTA TGG ACG, (SEQ ID NO: 1)
TCC TCA GGT AAG AAT GGC, (SEQ ID NO: 2)
ACC ATG TTC CGA GGG GAC, (SEQ ID NO: 3)
GAG CCA CAT TTG GAC GAG, (SEQ ID NO: 4)
AGT GAT GGC TGA GGA ATG, (SEQ ID NO: 5)
CTG TCC AAG TAT TTG AAA, (SEQ ID NO: 6)
GGC TGG AAA GAG AAC TGT, (SEQ ID NO: 7)
TCT GAA AGT GAT CTA CTG, (SEQ ID NO: 8)
TTC CGT TTC TAA AAT AAG, and (SEQ ID NO: 9)
GAT GCG TGG CTT CTG CTG (SEQ D NO: 10).

2. The oligodeoxynucleotide of claim 1, which is chemically modified.

3. The oligodeoxynucleotide of claim 2, which is chemically modified by incorporation of methylphosphonates, phosphoramidates, phosphorotriesters, phosphorothioates and/or phosphorodithioates therein.

4. The oligodeoxynucleotide of claim 2, which is chemically modified by incorporation of a cholesterol moiety at the 5'-terminus, the 3'-terminus or both the 5'-terminus and the 3'-terminus.

5. A composition, comprising the oligodeoxynucleotide of claim 1 and a pharmaceutically acceptable carrier.

6. An oligodeoxynucleotide, which has a length of 10 to 100 bases and which is complementary to a sequence of an antisense transcript complementing the J6 region of the immature mRNA of the IgH gene, wherein the oligonucleotide inhibits the activity of said antisense transcript.

7. The oligodeoxynucleotide of claim 6, which has a length of 15 to 30 bases.

8. The oligodeoxynucleotide of claim 6, which has a length of 18 bases.

9. The oligodeoxynucleotide of claim 6, which has a base sequence comprising a member selected from the group consisting of ACT ACT ACG GTA TGG ACG, (SEQ ID NO: 1)
TCC TCA GGT AAG AAT GGC, and (SEQ ID NO: 2)
ACC ATG TTC CGA GGG GAC (SEQ ID NO: 3).

10. The oligodeoxynucleotide of claim 6, which is chemically modified.

11. The oligodeoxynucleotide of claim 10, which is chemically modified by incorporation of methylphosphonates, phosphoramidates, phosphorotriesters, phosphorothioates and/or phosphorodithioates therein.

12. The oligodeoxynucleotide of claim 10, which is chemically modified by incorporation of a cholesterol moiety at the 5'-terminus, the 3'-terminus or both the 5'-terminus and the 3'-terminus.

13. A composition, comprising the oligodeoxynucleotide of claim 6 and a pharmaceutically acceptable carrier.

14. An oligodeoxynucleotide, which has a length of 10 to 100 bases and which is complementary to a sequence of an antisense transcript complementing the J6/E region of an immature mRNA of the IgH gene, wherein the oligonucleotide inhibits the activity of said antisense transcript.

15. The oligodeoxynucleotide of claim 14, which has a length of 15 to 30 bases.

16. The oligodeoxynucleotide of claim 14, which has a length of 18 bases.

17. The oligodeoxynucleotide of claim 14, which has a base sequence comprising a member selected from the group consisting of

GAG CCA CAT TTG GAC GAG, (SEQ ID NO: 4)

AGT GAT GGC TGA GGA ATG, (SEQ ID NO: 5)

CTG TCC AAG TAT TTG AAA, and (SEQ ID NO: 6)

GGC TGG AAA GAG AAC TGT (SEQ ID NO: 7).

18. The oligodeoxynucleotide of claim 14, which is chemically modified.

19. The oligodeoxynucleotide of claim 18, which is chemically modified by incorporation of methylphosphonates, phosphoramidates, phosphorotriesters, phosphorothioates and/or phosphorodithioates therein.

20. The oligodeoxynucleotide of claim 18, which is chemically modified by incorporation of a cholesterol moiety at the 5'-terminus, the 3'-terminus or both the 5'-terminus and the 3'-terminus.

21. A composition, comprising the oligodeoxynucleotide of claim 14 and a pharmaceutically acceptable carrier.

22. An oligodeoxynucleotide, which has a length of 10 to 100 bases and which is complementary to a sequence of an antisense transcript complementing the E region of an immature mRNA of the IgH gene, wherein the oligonucleotide inhibits the activity of said antisense transcript.

23. The oligodeoxynucleotide of claim 22, which has a length of 15 to 30 bases.

24. The oligodeoxynucleotide of claim 22, which has a length of 18 bases.

25. The oligodeoxynucleotide of claim 22, which has a base sequence comprising a member selected from the group consisting of

TCT GAA AGT GAT CTA CTG (SEQ ID NO: 8)

TTG CGT TTC TAA AAT AAG, and (SEQ ID NO: 9)

GAT GCG TGG CTT CTG CTG (SEQ ID NO: 10).

26. The oligodeoxynucleotide of claim 22, which is chemically modified.

27. The oligodeoxynucleotide of claim 26, which is chemically modified by incorporation of methylphosphonates, phosphoramidates, phosphorotriesters, phosphorothioates and/or phosphorodithioates therein.

28. The oligodeoxynucleotide of claim 26, which is chemically modified by incorporation of a cholesterol moiety at the 5'-terminus, the 3'-terminus or both the 5'-terminus and the 3'-terminus.

29. A composition, comprising the oligodeoxynucleotide of claim 22 and a pharmaceutically acceptable carrier.

* * * * *

UNITED STATES PATENT AND TRADEMARK OFFICE
CERTIFICATE OF CORRECTION

PATENT NO. : 6,140,492
DATED : October 31, 2000
INVENTOR(S) : Susanna Morelli, et al.

It is certified that error appears in the above-identified patent and that said Letters Patent is hereby corrected as shown below:

On the Title page, Items [73] and [30], are listed incorrectly.

Item [73], the Assignee information should read as follows:

---[73] Assignee: Consiglio Nazionale Delle Ricerche, Rome, Italy ---

Item [30], the foreign application priority data, should read as follows:

---[30], the foreign application priority data, should read as follows:

---[30] Foreign Application Priority Data

Mar. 3, 1995 [IT] Italy..................................M195 A 000419---

Signed and Sealed this

Nineteenth Day of June, 2001

Attest:

NICHOLAS P. GODICI
Attesting Officer
*Acting Director of the United States Patent and Trademark Office*